(12) United States Patent
Conger

(10) Patent No.: US 7,680,544 B1
(45) Date of Patent: Mar. 16, 2010

(54) FATIGUE RESISTANT DESIGN FOR LEADS EMPLOYING MULTI-STRAND CABLES AS PRIMARY CONDUCTORS

(75) Inventor: Steven R. Conger, Agua Dulce, CA (US)

(73) Assignee: Pacesetter, Inc., Sylmar, CA (US)

( * ) Notice: Subject to any disclaimer, the term of this patent is extended or adjusted under 35 U.S.C. 154(b) by 538 days.

(21) Appl. No.: 11/557,407

(22) Filed: Nov. 7, 2006

(51) Int. Cl.
*A61N 1/05* (2006.01)

(52) U.S. Cl. ........................ 607/122; 607/116

(58) Field of Classification Search ............... 607/119, 607/122, 125, 126, 127, 130; 361/776
See application file for complete search history.

(56) References Cited

U.S. PATENT DOCUMENTS

| 5,303,704 | A | 4/1994 | Molacek et al. |
|---|---|---|---|
| 5,483,022 | A | 1/1996 | Mar |
| 5,584,873 | A | 12/1996 | Shoberg et al. |
| 5,715,817 | A | 2/1998 | Stevens-Wright et al. |
| 5,800,496 | A | 9/1998 | Swoyer et al. |
| 5,935,159 | A | 8/1999 | Cross, Jr. et al. |
| 6,249,708 | B1 | 6/2001 | Nelson et al. |
| 6,483,022 | B1 | 11/2002 | Packard |
| 6,556,873 | B1 | 4/2003 | Smits |
| 6,999,821 | B2 | 2/2006 | Jenney et al. |
| 2004/0039434 | A1 | 2/2004 | Schrom et al. |
| 2005/0113899 | A1* | 5/2005 | Cross, Jr. ................. 607/122 |
| 2006/0041293 | A1 | 2/2006 | Mehdizadeh et al. |

FOREIGN PATENT DOCUMENTS

EP 1023915 2/2000

* cited by examiner

*Primary Examiner*—Carl H Layno
*Assistant Examiner*—Elizabeth K So

(57) ABSTRACT

A lead for connecting to a pacing and/or defibrillation power source is disclosed herein. The lead includes a lead tubular body, a connector for connecting the lead to the power source, and a strain-flex relief assembly joining the lead tubular body to the connector assembly and including a helical multi-strand cable conductor configuration.

15 Claims, 3 Drawing Sheets

FATIGUE RESISTANT DESIGN FOR LEADS EMPLOYING MULTI-STRAND CABLES AS PRIMARY CONDUCTORS

FIELD OF THE INVENTION

The present invention relates to medical apparatus and methods. More specifically, the present invention relates to pacing and defibrillation leads and methods of making and using such leads.

BACKGROUND OF THE INVENTION

The majority of new state of the art pacing and defibrillation leads incorporate multi-strand cables as primary conductors through the body of the lead. Such cables are non-stretchable and, as a result, are prone to premature fatigue failure in portions of a lead subject to repeated bending or sharp bends (e.g., lead connectors). The incidence of primary conductor failure due to bending stress tends to increase with the number of conductor cables employed in a lead.

There is a need in the art for a lead configuration that reduces the bending stress failure rate of multi-strand cable conductors employed as primary conductors in leads. There is also a need in the art for a method of using and manufacturing such a lead configuration.

BRIEF SUMMARY OF THE INVENTION

A pacing and/or defibrillation lead is disclosed herein. In one embodiment, the lead includes a tubular body and a cable conductor. The tubular body includes a flex-strain relief segment. The cable conductor includes a first length extending helically about a longitudinal axis of the tubular body through the flex-strain relief segment.

A lead for connecting to a pacing and/or defibrillation power source is disclosed herein. In one embodiment, the lead includes a lead tubular body, a connector for connecting the lead to the power source, and a strain-flex relief assembly joining the lead tubular body to the connector assembly and including a helical multi-strand cable conductor configuration.

A pacing or defibrillation lead is disclosed herein. In one embodiment, the lead includes a strain-flex relief assembly including a multi-strand cable conductor helically extending through the assembly.

A pacing or defibrillation lead is disclosed herein. In one embodiment, the lead includes means for relieving strain due to flexing of the lead. In one embodiment, the lead further includes means for orienting multi-strand cable conductors in a helical configuration.

A strain-flex relief assembly for a lead is disclosed herein. In one embodiment, the assembly includes a flexible tubular body including radially extending members having openings for receiving cable conductors and maintaining the cable conductors in a helical configuration.

A pacing or defibrillation lead is disclosed herein. In one embodiment, the lead includes a tubular body having a strain-flex relief assembly. Cable conductors extend through the assembly along a route that is non-parallel with a centerline of the lead.

A lead for connecting to a pacing and/or defibrillation power source is disclosed herein. In one embodiment, the lead includes a lead tubular body, a power source connector, and a strain-flex relief assembly. The power source connector connects the lead to the power source. The strain-flex relief assembly joins the lead tubular body to the power source connector assembly and includes a cable conductor and a flexible core. The flexible core includes a location feature for receiving the cable conductor and maintaining the cable conductor in a helical configuration. The location feature has a length, as measured in a direction generally parallel to a longitudinal axis of the flexible core, that is less than a length of the longitudinal axis of the flexible core.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
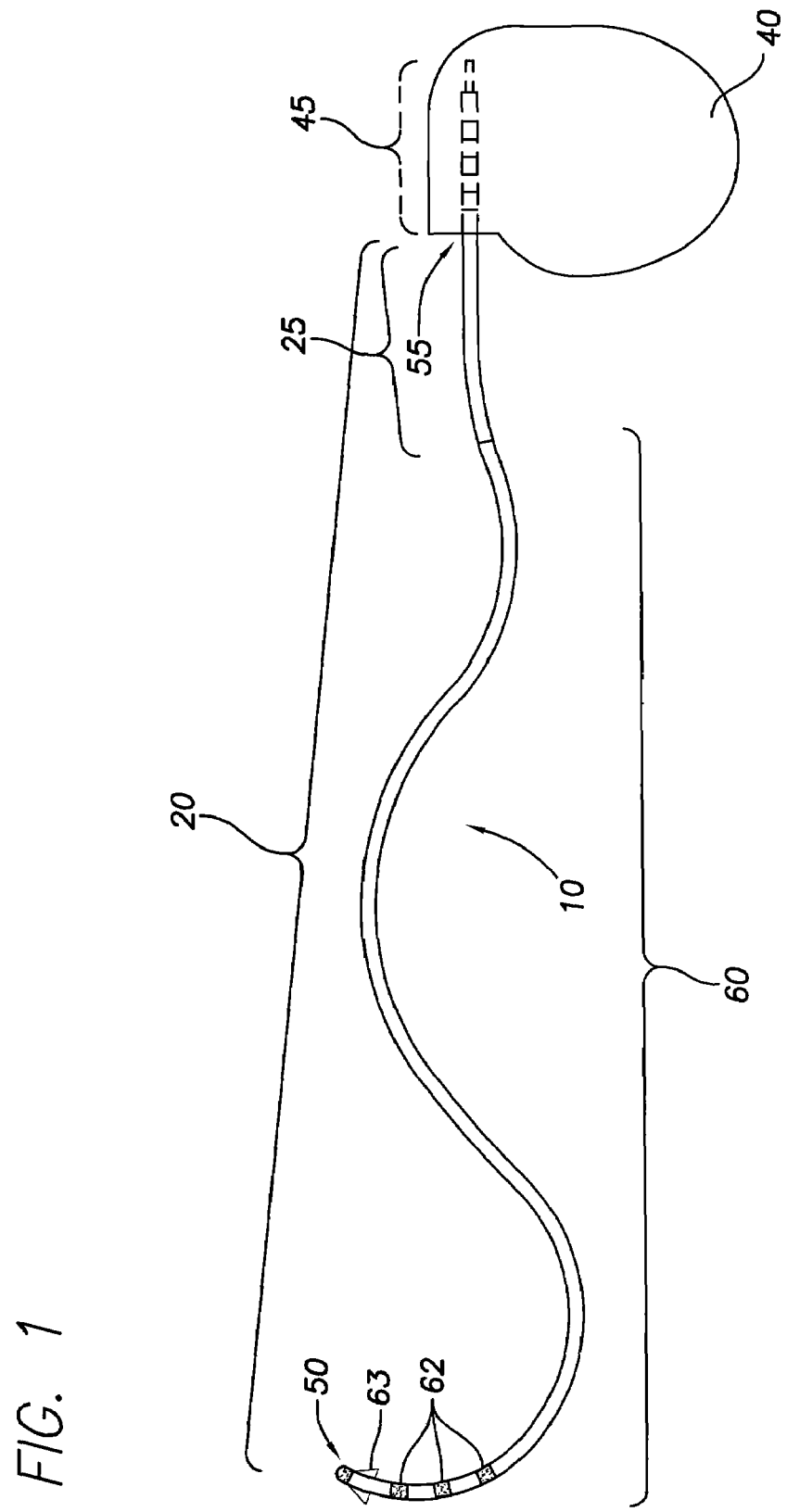
FIG. 1 illustrates the lead connected to a stimulation pulse generator of an implantable cardioverter-defibrillator ("ICD").

The present application describes a fatigue resistant design for pacing and/or defibrillation leads 10 that have multi-strand cable conductors 15a, 15b extending along the length of the tubular bodies 20 of such leads 10. The fatigue resistant lead 10 has a tubular body 20 that includes a flex-strain relief segment 25, which forms a portion of the length of the tubular body 20.

In one embodiment, the flex-strain relief segment 25 has a highly flexible longitudinally extending core 30. Along the length of the core 30, the multi-strand cable conductors 15a, 15b extend helically about a longitudinal axis of the core 30. By having its conductors 15a, 15b routed through the flex-strain relief segment 25 along a route that is non-parallel with the lead centerline, the conductors 15a, 15b are decoupled from the normal strains arising from flexing/bending of the lead tubular body 20. As a result, the flex-strain relief segment 25 advantageously reduces the fatigue failure rate for cable conductors 15a, 15b in lead tubular bodies 20 subject to repeated and sharp flexing.

For an overall discussion of one embodiment of a pacing and/or defibrillation lead 10 and an embodiment of its flex-strain relief segment 25, reference is made to FIG. 1, which illustrates the lead 10 connected to a stimulation pulse generator of an implantable cardioverter-defibrillator ("ICD") 40. As shown in FIG. 1, the lead 10 includes a tubular body 20 and a lead connector 45, which, in one embodiment, is received in (e.g., plugged into) the ICD 40 to connect the lead 10 to the ICD 40. The tubular body 20 includes a distal end 50, a proximal end 55, a conventional body segment 60, and a flex-strain relief segment 25. The proximal end 55 joins the distal end of the connector 45, and the distal end 50 includes electrodes 62 and fixation features 63 for affixing the distal end 50 to heart tissue.

As can be understood from FIG. 1, in one embodiment, the flex-strain relief segment 25 forms the segment of the tubular body 20 joining the connector 45 to the conventional body segment 60. In such a configuration, the flex-strain relief segment 25 forms the portion of the tubular body 20 that is immediately adjacent to the ICD and, as a result, is typically subject to the sharpest and most frequent bends.

In other embodiments, there will be one or more flex-strain relief segments 25 located at other locations along the length of the tubular body 20. For example, in one embodiment, the flex-strain relief segment 25 is located near the middle of the length of the tubular body 20. In another embodiment, the lead 10 has multiple flex-strain relief segments, one near the distal end 50, one near the middle of the tubular body 20, and one near the proximal end 55. Depending on the embodiment, the one or more flex-strain relief segments 25 will account for a greater or lesser extent of the length of the tubular body 20, as compared to the embodiment depicted in FIG. 1.

Figure 2:
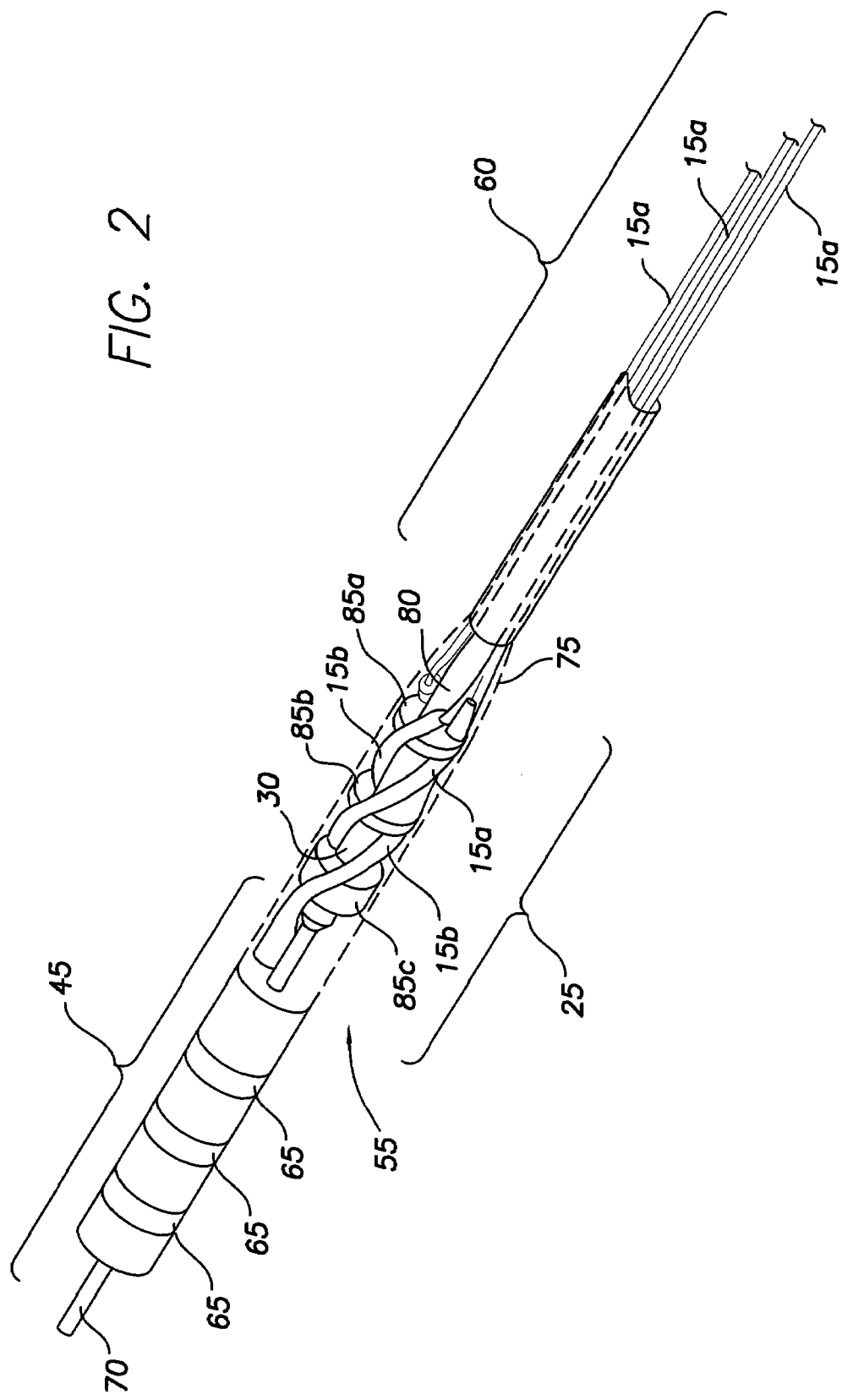
FIG. 2 is an enlarged isometric view of the connector, flex-strain relief segment and distal end of the conventional body segment.

For a detailed discussion of one embodiment of the flex-strain relief segment 25, reference is made to FIG. 2, which is an enlarged isometric view of the connector 45, flex-strain relief segment 25 and distal end of the conventional body segment 60. As shown in FIG. 2, the connector 45 includes conductor rings 65 and a conductor stem 70 that make electrical contact with electrical power sources within the ICD 40.

As indicated in FIG. 2, the conventional body segment 60 includes multi-strand sleeved cable conductors 15a, 15b (shown in phantom line where hidden within the conventional body segment 60 and solid line where visible due to the conventional body segment 60 being cut away). Along the length of the conventional body segment 60, the cable conductors 15a, 15b longitudinally extend through the conventional body segment 60 in a generally linear fashion.

As illustrated in FIG. 2, in one embodiment, the flex-strain relief segment 25 includes a flexible helix sleeve or core 30, a boot 75 (shown in hidden lines), and one or more multi-strand sleeved cable conductors 15a, 15b. Along the length of the core 30, the multi-strand cable conductors 15a, 15b extend helically about a longitudinal axis of the core 30. Thus, as one follows the lead 10 from the distal end 50 of the lead 10 to the proximal end of the connector 45, the cable conductors 15a, 15b extend generally linearly along the conventional body segment 60 until reaching the flex-strain relief segment 25, wherein the cable conductors 15a, 15b are helically routed along the flexible core 30. Upon reaching the distal end of the core 30, the cable conductors 15a, 15b return to a generally linear path as they extend along the connector 45 to electrically couple to their respective conductor rings 65 or conductor stem 70.

As can be understood from FIG. 2, the boot 75 extends about and encloses the helically routed cable conductors 15a, 15b and the flexible core 30. In one embodiment, the boot 75, in addition to enclosing the helically routed cable conductors 15a, 15b and the core 30, also extends over the distal end of the connector 45 and the proximal end of the conventional body segment 60. In one embodiment, the boot 75 serves to smoothly transition the surface of the connector 45 with the surface of the conventional body segment 60.

In one embodiment, the boot is formed of a polymer material such as silicone rubber, polyurethane, etc. and has a diameter of between approximately three millimeters and approximately four millimeters. In one embodiment, the boot is secured in place over the flex-strain relief segment 25 via a manufacturing method such as heat shrinking, adhesive bonding, overmolding, etc.

Figure 3:
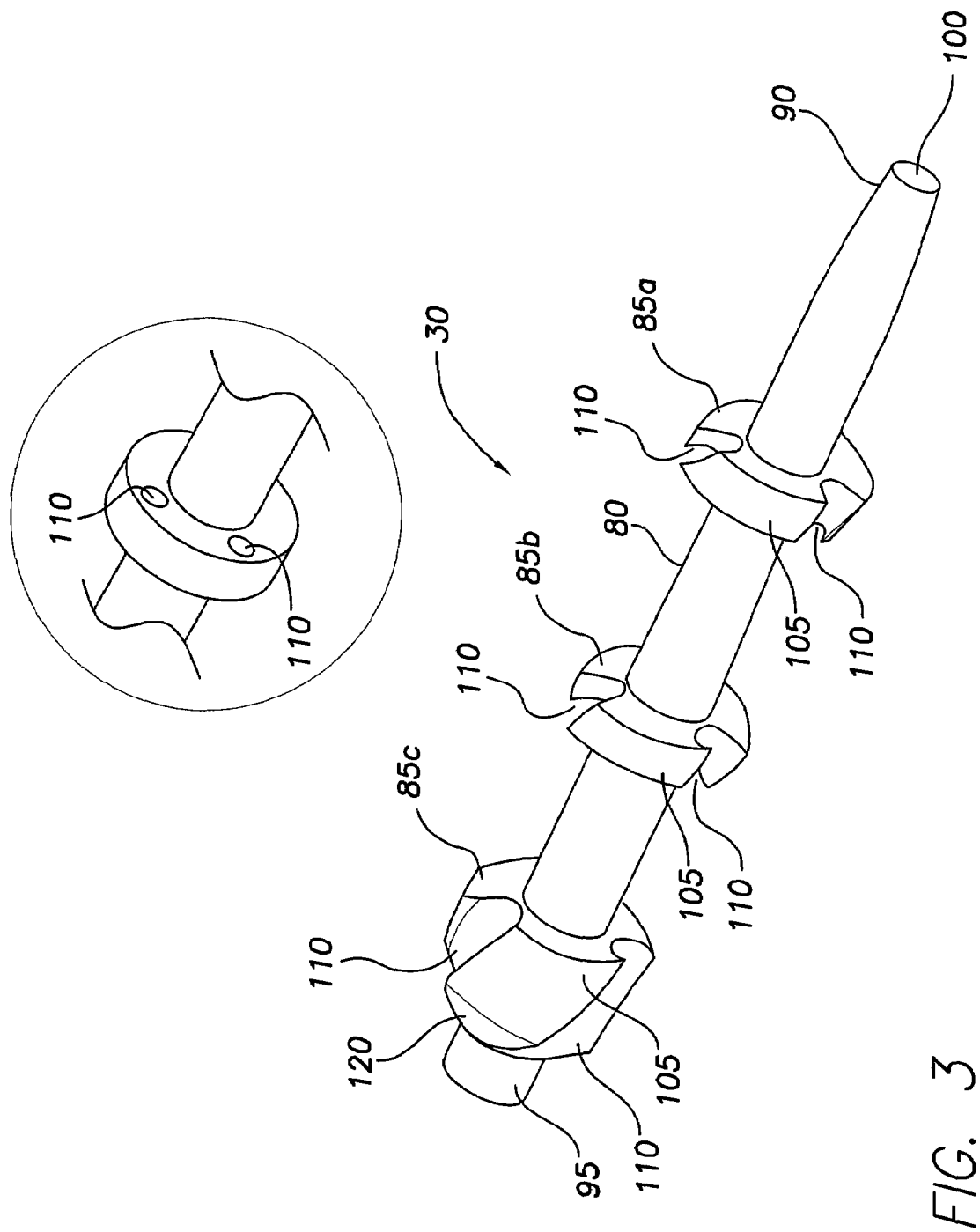
FIG. 3 is an enlarged isometric view of the flexible core employed in the flex-strain relief segment.

As indicated in FIG. 2 and more fully illustrated in FIG. 3, which is an enlarged isometric view of the flexible core 30, in one embodiment, the flexible core 30 includes a tubular body 80 and distal, middle and proximal radially extending discs or members 85a, 85b, 85c. The core tubular body 80 includes a distal end 90, a proximal end 95 and a lumen 100 extending longitudinally through the core 80. In one embodiment, to facilitate the joining of the core 80 to the conventional body segment 60, the core distal end 90 is more tapered in appearance as compared to the core proximal end 95, which has a larger diameter, more blunt appearance.

As depicted in FIG. 3, in one embodiment, each member 85a, 85b, 85c is a disc that perpendicularly radially extends from, and is centered about, the core tubular body 80. The outer circumferential surface 105 of each member 85a, 85b, 85c provides support for the boot 75 extending over the members 85a, 85b, 85c, as indicated in FIG. 2. As illustrated in FIG. 3, in one embodiment, the distal and middle radially extending members 85a, 85b are of generally equal thicknesses, while the proximal radially extend member 85c has a thickness two to three times the thickness of either of the other two members 85a, 85b.

In one embodiment, the most proximal member 85c has a relieved face 120 that forms the most proximal face of the member 85c. The relieved face 120 allows for termination access.

In one embodiment, the core 30 is formed from a solid block of molded silicone rubber, which provides a thicker wall for the core tubular body 80. This results in improved stiffness an support as compared to extruded tubing. Also, it provides superior strain relief.

In other embodiments, the members 85a, 85b, 85c have other shapes/configurations and/or locations along the core tubular body 80. Also, in other embodiments, there will be a greater or lesser number of members 85a, 85b, 85c along the length of the core tubular body 80. Regardless of the shape/configuration, number or location of the members 85a, 85b, 85c, in one embodiment, the members 85a, 85b, 85c serve as structures in which conductor-locating features 110 exist for the convenience of helically routing the conductors 15a, 15b through the flex-strain relief segment 25. In one embodiment, the members 85a, 85b, 85c are any shape/configuration that defines, or has defined in it, one or more conductor locating features 110 (e.g., notches, holes, bumps, protrusions, grooves, slots, etc.) that assist in the helical routing of the conductors 15a, 15b through the flex-strain relief segment 25. For example, in one embodiment, the members 85a, 85b, 85c are merely bumps on the outer circumferential surface of the core tubular body 80. The bumps serve as conductor locating features 110 for helically routing the conductors 15a, 15b through the flex-strain relief segment 25.

As indicated in FIG. 3, in one embodiment, the each member 85a, 85b, 85c and its respective notches or locating features 110 are thin as compared to the overall length of the core tubular body 80. In other words, each member 85a, 85b, 85c and its notches 110 have lengths, as measured in a direction generally parallel to the longitudinal axis of the flexible core 30, that are substantially less than the length of the longitudinal axis of the flexible core 30.

In one embodiment, the core 30 is formed of highly flexible polymer materials, such as silicone rubber, polyurethane, etc. In one embodiment, the core tubular body 80 has an outer diameter of between approximately 0.5 millimeter and approximately 1.5 millimeter. In one embodiment, the radially extending members 85a, 85b, 85c have a diameter of between approximately two millimeters and approximately four millimeters. In one embodiment, the radially extending members 85a, 85b, 85c are offset from each other by a distance of between approximately two millimeters and approximately ten millimeters. The offset distance between the members 85a, 85b, 85c helps to determine the pitch of the helical wind of the conductors 15a, 15b through the flex-strain relief segment 25.

While FIGS. 2 and 3 depict a core 30 having three members 85a, 85b, 85c, in other embodiments, the core 30 will have a greater or lesser number of members 85a, 85b, 85c. In one embodiment, the core 30 is simply the core tubular body 80 without any members 85a, 85b, 85c. In such a member-less embodiment, the conductors 15a, 15b are simply helically routed along the core 30 without the use of any conductor locating features 110. The member-less core 30 is formed from a polymer material such as silicone rubber, polyurethane, etc.

In one embodiment, the flex-strain relief segment 25 does not have a core 30 as depicted in FIGS. 2 and 3. Instead, the conductors 15a, 15b are helically routed about a typical core portion of a typical lead 10, wherein the typical core portion extends generally uninterrupted from the conventional body segment 60 of the lead 10 into the flex-strain relief segment 25. In one embodiment, the conductors 15a, 15b are helically routed about a central tubular body of a lead 10 that forms a central lumen of the lead 10 and extends generally uninterrupted from the conventional body segment 60 of the lead 10 into the flex-strain relief segment 25.

As shown in FIG. 3, in one embodiment, each radially extending member 85a, 85b, 85c includes one or more conductor locating features 110. As mentioned above, in one embodiment, the conductor locating features 110 are any shape/configuration (e.g., notches, bumps, protrusions, grooves, slots, etc.) defined on or in a member 85a, 85b, 85c that assist in the helical routing of the conductors 15a, 15b through the flex-strain relief segment 25.

In one embodiment, the conductor locating features 110 are arcuately shaped notches 110. As can be appreciated from inspection of FIGS. 2 and 3, the cable conductors 15a, 15b are received in each notch 110. Each notch 110 provides a snap-fit for retaining its respective cable conductor 15a, 15b.

In one embodiment, the notches 110 open through the outer circumferential surface 105 of the radially extending members 85a, 85b, 85c. In other embodiments, the conductor locating features 110 are holes extending through the radially extending members 85a, 85b, 85c such that the cable conductors 15a, 15b must be threaded through the holes during lead assembly, as opposed to being snapped into a notch 110.

In one embodiment, the bottom or inner surfaces of the notches 110 are offset from the outer circumferential surface of the core tubular body 80 because the notch depths are less than the radial distance between the outer circumferential surface of the members 85a, 85b, 85c and the outer circumferential surface of the core tubular body 80. As a result, the cable conductors 15a, 15b are generally offset by a similar distance from the outer circumferential surface of the core tubular body 80.

In another embodiment, the bottom or inner surfaces of the notches 110 are generally flush with the outer circumferential surface of the core tubular body 80. In other words, there is no offset between the notch 110 and the outer circumferential surface of the core tubular body 80. As a result, the cable conductors 15a, 15b generally helically extend against the outer circumferential surface of the core tubular body 80.

As illustrated in FIGS. 2 and 3, in one embodiment, the axis of each conductor locating feature or opening 110 in the members 85a, 85b, 85c, whether the opening 110 is a notch 110, hole, etc., is slanted or pitched relative to the longitudinal axis of the core tubular body 80. In one embodiment, the pitch angle (i.e., the angle of deviation between the axis of the notch 110 and the longitudinal axis of the core tubular body 80) is between approximately 10 degrees and approximately 60 degrees.

As can be understood from FIG. 2, because the cable conductors 15a, 15b are received in the conductor locating features 110 and the conductor locating features 110 are pitched relative to the longitudinal axis of the core tubular body 80, the cable conductors 15a, 15b are maintained in a helical arrangement having a pitch generally equal to the pitch of the notches 110. Thus, the conductor locating features 110 are used to locate and maintain the cable conductors 15a, 15b in a helically pitched and spaced arrangement relative to each other. In addition to helping to maintain the helical arrangement of cable conductors 15a, 15b when the lead 10 is being used, the conductor locating features 110 of the core 30 maintain the cable conductors 15a, 15b in the helical arrangement during assembly of the lead 10.

While in various embodiments the conductor locating features 110 will have a pitch as discussed above, in other embodiments, the conductor locating features 110 will not have a pitch. Regardless, the conductor locating features 110 will still be able to locate and hold the conductors 15a, 15b in a helical arrangement in the flex-strain relief segment 25.

In one embodiment, the conductors 15a, 15b will be routed through the flex-strain relief segment 25 in a helical configuration having a pitch of between approximately 10 degrees and approximately 60 degrees. In other embodiments, the helical configuration of the conductors will have a pitch that is greater or lesser than the aforementioned range.

In one embodiment, an inner conductor coil is routed through the core lumen 100, the core proximal end 95 is secured to the distal end of the connector 45 via medical adhesive tack bonds, the core distal end 90 is secured to the proximal end of the lead body 60 via medical adhesive tack bonds, and the conductors 15a, 15b are snapped into the locating notches 110. The sleeve is then pulled over the flex region 25 of the lead body 20.

As can be understood from FIG. 2, the helical cable conductor arrangement of the flex-strain relief segment 25 is advantageous because it allows the lead 10 to bend repeatedly and sharply at the relief segment 25 without requiring the cable conductors 15a, 15b to stretch or compress. The helical cable conductor arrangement provides a reduction in normal stress by decoupling axial cable conductor force from the lead bending force. As a result, a lead 10 having the disclosed flex-strain relief segment 25 offers a reduced rate of cable conductor failure, as compared to leads not having the relief segment 25.

Although the present invention has been described with reference to preferred embodiments, persons skilled in the art will recognize that changes may be made in form and detail without departing from the spirit and scope of the invention.

What is claimed is:

1. A lead comprising:
   a tubular body including a flex-strain relief segment and a conventional body segment; and
   a conductor cable including a first length and a second length, the first length extending helically about a longitudinal axis of the tubular body through the flex-strain relief segment, the second length joining the first length and extending longitudinally along the conventional body segment of the tubular body in a generally linear fashion;
   wherein the flex-strain relief segment includes a flexible core and at least a portion of the flexible core is shaped into a locating feature for receiving a portion of the first length.

2. The lead of claim 1, wherein the locating feature is a notch.

3. The lead of claim 1, wherein the locating feature is a hole.

4. The lead of claim 1, wherein the flexible core further includes a radially extending member and the locating feature is formed in the member.

5. The lead of claim 4, wherein the locating feature opens in the outer radial edge of the member.

6. The lead of claim 1, wherein the flexible core includes a longitudinally extending lumen.

7. The lead of claim 1, wherein the flexible core extends from a conventional body segment of the tubular body, the conventional body segment being next to the flex-strain relief segment.

8. The lead of claim 1, wherein the flexible core is formed from silicone rubber or polyurethane.

9. A lead comprising:
a tubular body including a flex-strain relief segment and a conventional body segment; and
a conductor cable including a first length and a second length, the first length extending helically about a longitudinal axis of the tubular body through the flex-strain relief segment, the second length joining the first length and extending longitudinally along the conventional body segment of the tubular body in a generally linear fashion;
wherein the flex-strain relief segment includes a flexible core, wherein the flexible core comprises a locating feature that is coaxial to the tubular body and offset in a radial direction from the tubular body, and wherein the locating feature is angled relative to the longitudinal axis and assists in providing a helical pitch for the first length.

10. A lead for connecting to a pacing and/or defibrillation power source, the lead comprising
a lead tubular body;
a power source connector for connecting the lead to the power source; and
a strain-flex relief assembly joining the lead tubular body to the power source connector, wherein the strain-flex assembly includes:
a helical cable conductor configuration; and
a flexible core, wherein at least a portion of the flexible core is shaped into at least two locating features spaced apart from each other along the length of the flexible core, the at least two locating features each receiving a portion of the helical cable conductor configuration.

11. The lead of claim 10, wherein the core includes at least two radially extending members spaced apart from each other along the length of the flexible core and wherein each member includes one of the locating features.

12. The lead of claim 10, further comprising a generally linear multi-strand cable conductor configuration extending longitudinally through the lead tubular body and joining the helical multi-strand cable conductor configuration.

13. A lead for connecting to a pacing and/or defibrillation power source, the lead comprising:
a lead tubular body;
a power source connector for connecting the lead to the power source; and
a strain-flex relief assembly joining the lead tubular body to the power source connector assembly, wherein the strain-flex assembly includes:
a cable conductor; and
a flexible core, at least a portion of which is shaped into a location feature for receiving the cable conductor and maintaining the cable conductor in a helical configuration, wherein the location feature has a length, as measured in a direction generally parallel to a longitudinal axis of the flexible core, that is less than a length of the longitudinal axis of the flexible core.

14. The assembly of claim 13, wherein the location feature is pitched relative to the longitudinal axis of the tubular body.

15. The assembly of claim 13, wherein the flexible core further includes a radially extending member including the location feature and wherein the member has a length, as measured in a direction generally parallel to the longitudinal axis of the flexible core, that is less than the length of the longitudinal axis of the flexible core.

* * * * *